United States Patent [19]
Kawashima et al.

[11] Patent Number: 5,908,879
[45] Date of Patent: Jun. 1, 1999

[54] COATED METAL FLUORIDE PARTICLES AND A DENTAL COMPOSITION CONTAINING COATED METAL FLUORIDE PARTICLES

[75] Inventors: Mitsunobu Kawashima; Kenichi Hino, both of Kurashiki, Japan

[73] Assignee: Kuraray Co., Ltd., Kurashiki, Japan

[21] Appl. No.: 08/900,838

[22] Filed: Jul. 25, 1997

[30] Foreign Application Priority Data

Jul. 25, 1996 [JP] Japan ..................................... 8-196025

[51] Int. Cl.$^6$ ................................ C08K 9/06; C08K 5/24
[52] U.S. Cl. ........................ 523/212; 523/116; 523/118; 523/213; 524/263; 524/265; 524/436; 524/858; 428/405
[58] Field of Search ..................................... 523/116, 118, 523/212, 213; 524/263, 265, 436, 858; 428/405

[56] References Cited

U.S. PATENT DOCUMENTS

| | | | |
|---|---|---|---|
| 4,407,984 | 10/1983 | Ratcliffe et al. | 523/116 |
| 4,882,225 | 11/1989 | Fukui et al. | 428/405 |
| 5,154,762 | 10/1992 | Mitra et al. | 523/116 |
| 5,670,258 | 9/1997 | Mitra et al. | 428/405 |

*Primary Examiner*—Andrew E. C. Merriam
*Attorney, Agent, or Firm*—Oblon, Spivak, McClelland, Maier & Neustadt, P.C.

[57] ABSTRACT

A coated particle is described, which includes a metal fluoride particle and a polysiloxane coating on the surface of the particle. A dental composition is also described, which includes the coated particle, a polymerizable monomer, and a polymerization initiator.

19 Claims, 1 Drawing Sheet

COATED METAL FLUORIDE PARTICLES AND A DENTAL COMPOSITION CONTAINING COATED METAL FLUORIDE PARTICLES

BACKGROUND OF THE INVENTION

1. Field of the Invention

The present invention relates to a coated metal fluoride particle suited for use in dental materials for the prevention of caries by strengthening the tooth substrate, and to a dental composition incorporating the metal fluoride particle.

2. Discussion of the Background

The effect of fluoride ions to strengthen the tooth substrate in dental treatment is already well known, and the treatment of the tooth substrate with fluoride ions to prevent and/or inhibit tooth caries is performed routinely.

In recent years, restorative resins have been employed as materials for tooth restoration. However, in the unfortunate case that a gap forms between the tooth substrate and the restorative material, leaks can occur around the margins and bacteria can penetrate into the gap between the tooth substrate and the restorative material and cause secondary caries.

Dental restorative resins that contain a fluoride compound have been proposed with the aim of preventing secondary caries by strengthening the tooth substrate through the fluorination of the tooth substrate around the wall of the cavity by fluoride ions which elute from the fluoride compound (Japanese Patent Application Publication No. Sho 48-80151 and No. Sho 50-49358).

Conventionally, metal fluorides such as sodium fluoride, fluorides of ammonium salts such as ammonium fluoride, and fluorine containing glasses such as fluoroaluminosilicate glass are known to release fluoride ions. However, with metal fluorides and fluorides of ammonium salts, although the amount of released fluoride ions is high and subsequent fluorination of the tooth substrate by the release of fluoride ions into the surrounding tooth substrate can be realized, there is the problem that a large decrease in the mechanical properties and adhesive performance of the restorative resin itself accompanies the elution of fluoride ions, causing further fracture and shedding of the restorative resin. On the other hand, with fluorine containing glasses, although there is no decrease in the mechanical properties or adhesion performance of the dental restorative resin incorporating the glass, there is the problem that the amount of fluoride ions eluted is small.

In order to provide a fluoride ion releasing dental composition having excellent durability and high practical value, there is a need to develop a fluoride ion releasing material which elutes fluoride ions in large amounts but which does not reduce the mechanical properties or adhesion performance of the restorative material itself.

The inventors of the present invention considered that when a fluoride compound is incorporated into a restorative resin to supply fluoride ions to strengthen the tooth substrate for preventing secondary caries, it is desirable that the fluoride compound elutes fluoride ions in large amounts. From this point of view, the inventors of the present invention selected in particular metal fluorides from the large number of different fluoride compounds, and studied their incorporation into dental restorative materials.

When the relationship between the amount of fluoride ions eluted and the decrease in mechanical properties and adhesion performance was investigated for dental restorative materials incorporating metal fluorides, it was observed that although the amount of fluoride ions eluted increased with an increasing amount of metal fluoride incorporated, the mechanical properties and adhesion performance is adversely effected with the increasing amount of metal fluoride incorporated. From these findings, it was considered that it would be possible to inhibit the decrease in mechanical properties and adhesion performance of the restorative resin by controlling the speed of elution of the metal fluorides incorporated therein.

However, if the sole objective is to simply control the speed of elution of fluoride ions from the dental restorative resin having the metal fluorides incorporated therein, it can be achieved by the conventional technique of microencapsulation. As described in "Kobunshi Daijiten" (1994, Maruzen Kabushiki Kaisha) and "Shinpan Kobunshi Jiten" (1988, Asakura Shoten), microencapsulation involves coating the surface of a core material such as small solid particles, liquid drops, or gas bubbles to seal it, thereby protecting the core material from the external environment, and controlling the speed at which the core material is eluted to the outside. By adopting a metal fluoride as the core material and coating the surface thereof, it is possible to control the speed of elution of the metal fluoride.

The technique of microencapsulating fluoride compounds is disclosed in Japanese Patent Publication No. Hei 2-31049. However, it is used there with the aim of preventing the elution of fluoride ions from the fluoride compound in order to inhibit reactions with other components in the same system. It is thus used as "protection for the core material" as mentioned in the above description of the microencapsulation technique, which is completely different from the objective in the present invention which requires that the coating acts to actively cause fluoride ions to be eluted.

Furthermore, there is disclosed in Japanese Patent Application Publication No. Sho 58-99409 a fluoride-containing aluminosilicate glass powder whose surface in coated with a soluble polymer. When a powder coated with a soluble polymer is used in a dental restorative material, under the damp conditions found inside the oral cavity, the soluble polymer is washed away by saliva or water taken into the mouth during eating and drinking, which necessarily limits its coating function with respect to the powder over a long period of time and is thus unable to fulfill the objective of the present invention, which is to ensure retention of mechanical properties and adhesion performance of a restorative material containing fluoride particles.

It is common for the fluoride compound to be incorporated into the dental composition in its powder form, rather than being dissolved in the dental composition (Japanese Patent Application Publication No. Sho 48-80151 and No. Sho 50-49358). It is also common for the powder filler to be subjected to a surface treatment such as silane coupling treatment before being incorporated into the dental composition. Of course, the treatment of the metal fluoride with a silane coupling agent would easily be considered, and it can be anticipated that the treatment of the metal fluoride with a silane coupling agent would control elution of the metal fluoride. However, the effect desirable in the present invention cannot be achieved simply by subjecting the metal fluoride to silane coupling treatment.

Studies by the inventors of the present invention with respect to the problem of actively promoting the release of fluoride ions when incorporating a metal fluoride into a dental composition for preventing secondary caries via fluoride ions, whilst avoiding any decrease in the mechanical properties and adhesion performance of the dental restorative resin accompanied with the elution of fluoride ions, have shown that the two requirements cannot be satisfied at the same time with the fluoride compounds obtained by conventional techniques, and that there are thus problems with applying the conventional techniques to dental compositions in the present invention.

The inventors of the present invention carried out research into producing a fluoride particle by which the contradictory requirements in the prior art (i.e., avoiding any inhibition of the speed of elution of the fluoride ions whilst inhibiting the decrease in the mechanical properties and adhesion performance of the dental composition containing the fluoride compound) could both be satisfied. As a result, they found that this objective could be realized by a fluoride particle obtained by coating a metal fluoride with a polysiloxane.

At the start of their research, the inventors of the present invention anticipated that this would have the same result as the conventional microencapsulation technique, i.e., that the elution of the metal fluoride would be inhibited by coating the metal fluoride particle with a polysiloxane, whereby the decrease in the mechanical properties and adhesion performance would also be reduced. However, detailed studies by the inventors of the present invention showed that, contradictory to this expectation, the amount of fluoride ions eluted did not decrease when the metal fluoride was coated with a polysiloxane, and that in fact the amount of fluoride ions was rather increased by coating with a polysiloxane.

This favorable phenomenon that not only was it possible to inhibit any decrease in the mechanical properties and adhesion performance of the dental composition by microencapsulating the metal fluoride with a polysiloxane compound, but also that the amount of fluoride ions eluted could be increased, could not have been anticipated from conventional teachings.

Although the technique of coating inorganic powders with a polysiloxane is disclosed in Japanese Patent Application Publications No. Hei 7-331112 and No. Hei 8-3473, there is no mention whatsoever in these publications of using metal fluorides as the inorganic powder. Furthermore the teaching of these publications is that an improvement in the bonding force between the inorganic powder and the resin and another improvement in the adhesion between inorganic powder particles can be realized with a mixture of an inorganic powder and a resin, from which it would not have been possible to infer the objective of the present invention.

SUMMARY OF THE INVENTION

One object of the present invention is to provide a dental composition that strengthens the teeth.

Another object of the present invention is to provide a dental composition that prevents secondary caries.

Another object of the present invention is to provide a fluoride particle that is suitable for use in dental composition that elutes fluoride in large amounts.

Another object of the present invention is to provide a fluoride particle that is suitable for use in dental compositions that does not reduce the mechanical properties and adhesion performance of the dental composition.

These and other objects of the present invention have been solved by coating a metal fluoride particle with a polysiloxane.

One embodiment of the present invention is to provide a coated particle, which includes:

(i) a particle including a metal fluoride; and (ii) a coating on the surface of said particle, said coating including a polysiloxane.

Another embodiment of the present invention is to provide a coated particle, which includes the reaction product of a reaction mixture including:

a particle including a metal fluoride; and a silanol compound obtained by hydrolysis or partial hydrolysis of a silane compound having the general formula (I):

wherein $R^1$ is an organic group having no more than 8 carbons, X is a halogen, $R^2$ is an organic group having no more than 6 carbon atoms, l and m are integers 0 or 1, whose sum is 1, and n is an integer of 0 or 1.

Another embodiment of the present invention is to provide a method, which includes:

contacting a particle including a metal fluoride with a silanol compound obtained by hydrolysis or partial hydrolysis of a silane compound having the general formula (I):

wherein $R^1$ is an organic group having no more than 8 carbons, X is a halogen, $R^2$ is an organic group having no more than 6 carbon atoms, l and m are integers of 0 or 1, whose sum is 1, and n is an integer of 0 or 1; and allowing the silanol to undergo a condensation reaction.

Another embodiment of the present invention is to provide a dental composition, which includes: (a) a metal fluoride particle having a polysiloxane layer on its surface; (b) a polymerizable monomer; and (e) a polymerization initiator.

By coating the surface of the metal fluoride particle with a polysiloxane, there is no inhibition of the speed of elution of the fluoride ions, and when it is incorporated into a dental restorative resin there is substantially no reduction in the mechanical properties or adhesion performance of the restorative material when fluoride ions are eluted from the dental restorative resin, and it is thus possible to solve such problems as fracture and shedding of the restorative material.

BRIEF DESCRIPTION OF THE PREFERRED EMBODIMENTS

Figure 1:
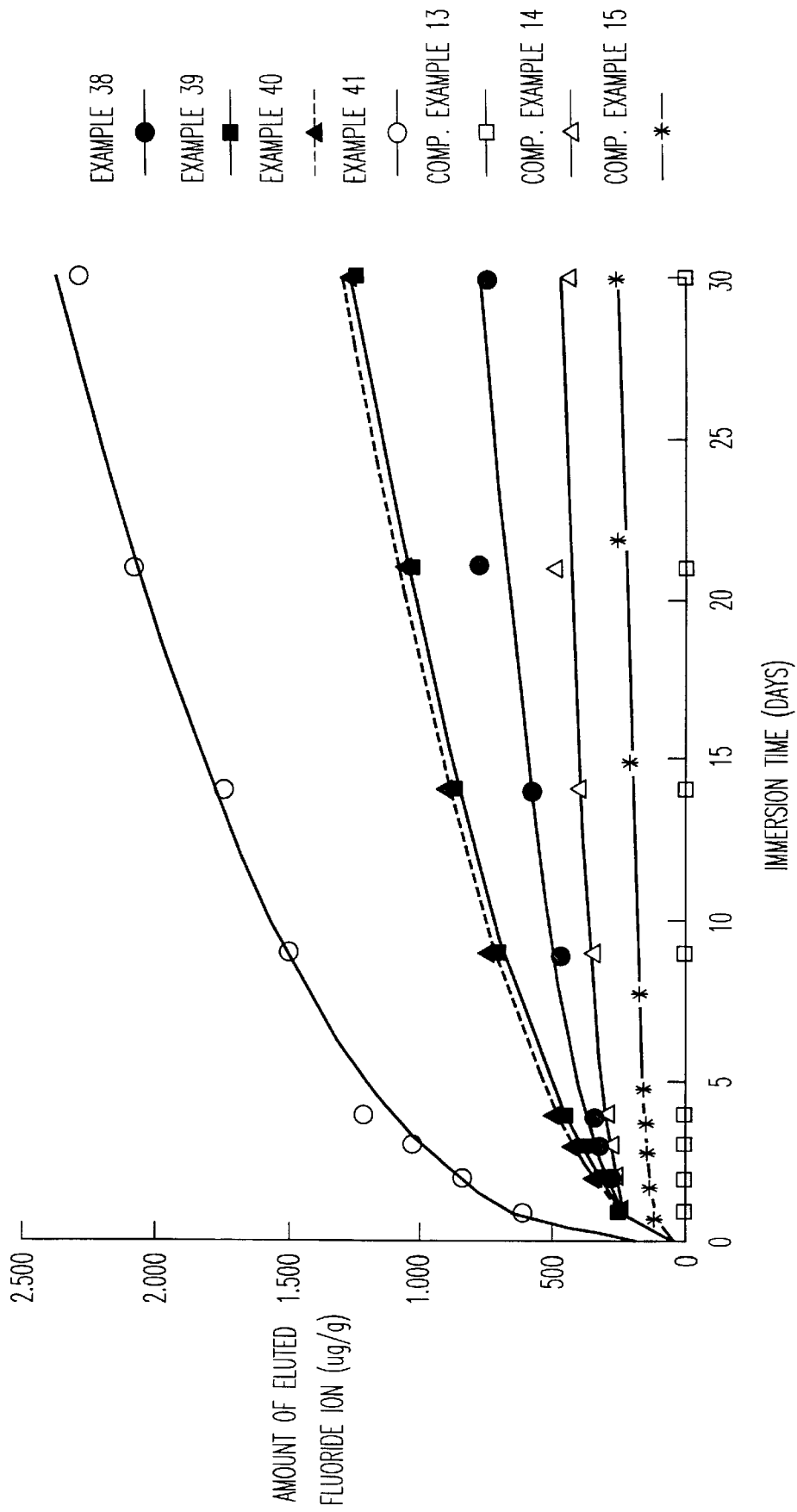
FIG. 1 is a graph showing the amount of fluoride ions eluted vs. immersion time for several examples and comparative examples.

Other features of the present invention will become apparent in the course of the following descriptions of exemplary embodiments, which are given for illustration of the invention and are not intended to be limiting thereof.

The present invention thus involves a metal fluoride particle having a polysiloxane layer on its surface. Preferably, the present invention provides a fluoride ion releasing dental composition that includes: (a) a metal fluoride particle having a polysiloxane layer on its surface; (b) a polymerizable monomer; and (c) a polymerization initiator.

Any metal fluoride can be used in the present invention provided it is soluble in water and releases fluoride ions. Examples include lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, diamine silver fluoride, sodium hydrogen fluoride, ammonium hydrogen fluoride, potassium hydrogen fluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorodistannate (II), and potassium hexafluorozirconate.

The fluorides of the metals of Groups 1 and 2 of the Periodic Table: lithium fluoride, sodium fluoride, potassium fluoride, rubidium fluoride, cesium fluoride, beryllium fluoride, magnesium fluoride, calcium fluoride, strontium fluoride, and barium fluoride are preferred, and sodium fluoride is the most preferred. These metal fluorides can be used singularly or in combinations of two or more.

The form or shape of the metal fluoride is not particularly limiting, and thus any of the particulate form, needle form, fiber form or plate form can be used. The size of the compound also and is thus not subject to any particular limitations. However, given that the fluoride particle of the present invention is obtained by coating the particles with polysiloxane, it is necessary to take into consideration the fact that the fluoride particle will become larger than the starting metal fluoride. When the fluoride particle of the present invention is to be incorporated into a dental restorative resin, it is preferred from the point of view of usability of the dental restorative resin to prepare a metal fluoride particle having a size of no more then 0.5 mm and preferably no more than 0.05 mm. These ranges include all values and subranges therebetween.

The polysiloxane used in the present invention preferably refers to a compound having a molecular structure in which —Si—O— bonds are cross-linked, and the term "polysiloxane" used in the present invention preferably includes organopolysiloxanes in which one of the bonding sites of the silicon atoms is bonded to an organic group instead of an oxygen atom. The polysiloxane may be obtained by the dehydration or condensation of silane compounds having silanol groups. The dehydration may be conducted under vacuum or by heating, or both. More preferably, they are obtained by the intermolecular condensation of silanol compounds which are obtained by the hydrolysis or partial hydrolysis of silane compounds.

The following preferred methods can be used to coat the surface of the metal fluoride particle with polysiloxane. The step of hydrolyzing the above-mentioned silane compounds and subsequent condensation to give a polymer can be carried out by conventional methods, (1) A silanol compound obtained by the hydrolysis of hydrolyzable groups of a silane compound is coated onto the metal fluoride, followed by condensation of silanol groups between siloxane molecules.

The following method is preferred: To an organic solvent which is miscible with water such as methanol, ethanol, t-butanol etc. the silane compound is added together with water in an amount necessary for the hydrolysis or partial hydrolysis of the silane compound, and the silane compound is hydrolyzed in the presence of an acid catalyst to prepare a solution of an organic solvent containing the hydrolyzed product. The metal fluoride is then added to this solution, and the organic solvent is evaporated by heating or under vacuum to give a metal fluoride powder having the hydrolyzed product adhered to its surface. A metal fluoride powder coated with polysiloxane can then be obtained by adding an acid or base to the powder if necessary, and heating the same to effect the condensation reaction of the silanol. The molecular structure of the polysiloxane can be confirmed by the infrared absorption spectrum of the coating on the metal fluoride.

Alternatively, an excess of water is added to the silane compound and hydrolysis is carried out in the presence of an acid catalyst; whereafter the hydrolyzed product is extracted from the aqueous layer with an organic solvent non-miscible with water such as ethyl acetate, ethyl other, chloroform, methylene chloride. The metal fluoride is then added to the solution containing the above hydrolyzed product, and the organic solvent is subsequently removed by heating or under vacuum to give a metal fluoride powder having the hydrolyzed product adhered to its surface. The metal fluoride powder coated with polysiloxane can then be obtained by adding an acid or base to the powder if necessary, and heating the same to effect the condensation reaction of the silane.

(2) A silane compound is subjected to hydrolysis and followed by intermolecular condensation of silanol groups to obtain a polymer which is then coated onto the metal fluoride.

The following method is preferred. A specified amount of water is added to a silane compound and hydrolysis is carried out in the presence of an acid catalyst. By eliminating the alcohol produced as a side product, the silane compound condenses to give oligomers of the silane compound. These oligomers are then added to the metal fluoride powder so that they adhere the surface of the metal fluoride powder, and a metal fluoride powder coated with polysiloxane can then be obtained by adding an acid or base to the powder if necessary, and heating the same to effect the condensation reaction of the silanol groups of the oligomers.

Any silane compound can be used as the starting material for the polysiloxane of the present invention provided it produces silanol groups upon hydrolysis, and can give a polysiloxane by subsequent intermolecular condensation of the silanol groups of these silanol compounds. Silane compounds represented by the following general formula:
General Formula I $$[(R^1O)_l(X)_m]_{4-n}\text{—SiR—R}^2{}_n \tag{I}$$

wherein $R^1$ is an organic group having no more than 8 carbon atoms, X is a halogen, $R^2$ is an organic group having no more than 6 carbon atoms, l and m are integers 0 or 1 whose sum equals 1, and n is an integer 0 or 1 are particularly preferred. More preferably, $R^1$ is an alkyl, aryl, alkenyl, or alicyclic group that may be substituted or unsubstituted.

In general formula I, the $R^1O$ group and the X group are functional groups or atoms which can produce silanol groups. Specific examples of $R^1$ include methyl, ethyl, 2-chloroethyl, allyl, aminoethyl, propyl, isopentyl, hexyl, 2-methoxyethyl, phenyl, m-nitrophenyl, and 2,4-dichlorophenyl; and specific examples of X include chlorine and bromine. Of these, methyl and ethyl groups are preferred for $R^1$, and chlorine is preferred for X.

It is preferred that $R^2$ be an organic group having no more than 6 carbon atoms. More preferably, $R^2$ is an alkyl, aryl, alkenyl, or alicyclic group that may be substituted or unsubstituted. Specific examples include methyl, chloromethyl, bromomethyl, ethyl, vinyl, 1,2-dibromovinyl, 1,2-dichloroethyl, 2-cyanoethyl, diethylaminoethyl, 2-aminoethylaminoethyl, 2-(2-aminoethylthioethyl), propyl, isopropyl, 3-hydroxypropyl, 3-mercaptopropyl, 3-aminopropyl, 3,3,3-trifluoropropyl, 3-glycidoxypropyl, 3-(2-aminoethylaminopropyl), allyl, n-butyl, isobutyl, hexyl, cyclohexyl and phenyl. In particular, methyl, ethyl, propyl, vinyl and phenyl are preferred.

Examples of silane compounds wherein n=0 in general formula (I) include tetramethoxy silane, tetraethoxy silane, tetraallyloxy silane, tetrabutoxy silane, tetrakis (2-ethylhexyloxy)silane, diethoxy dichlorosilane, tetraphenoxy silane, tetrachlorosilane. Of these, tetramethoxy silane and tetraethoxy silane are particularly preferred.

Examples of silane compounds wherein n=1 in general formula I include methyl trimethoxy silane, ethyl triethoxy silane, methoxy tripropyl silane, propyl triethoxy silane, hexyl trimethoxy silane, vinyl triethoxy silane, 3-methacryloyloxypropyl trimethoxy silane, 3-methacryloyloxypropyl dimethoxy methyl silane, vinyl triethoxy silane, 3-aminopropyl triethoxy silane, methyl trichloro silane and phenyl trichloro silane. Of these, methyl trimethoxy silane, ethyl triethoxy silane, vinyl triethoxy silane, 3-methacryloyloxypropyl dimethoxy methyl silane and phenyl trichloro silane are particularly preferred. These compounds can be used singularly or in combinations of two or more.

It is preferred to coat 100 parts by weight of the metal fluoride with at least 20 parts by weight of polysiloxane, and further preferably with at least 50 parts by weight of polysiloxane. These ranges include all values and subranges therebetween. On the other hand, there are no particular limitations with respect to the upper limit for the amount of the coating, but given the facts that (a) the effect is saturated and there is no further enhancement of the effect even if the amount of coating is increased beyond 500 parts by weight of polysiloxane per 100 parts by weight of the metal fluoride, and (b) if the proportion of polysiloxane becomes high the proportion of metal fluoride becomes relatively lower with a consequent substantial reduction in the amount of fluoride ions released, it is preferred to take 500 parts by weight as the upper limit.

The structure of the metal fluoride particles of the present invention can have any form, but preferably one in which substantially the entire surface of the metal fluoride particle is coated with polysiloxane. The coating may be adhered to, or coated on, or bonded to the surface via chemical or physicochemical or physical interactions. It may have a single core structure in which a single metal fluoride particle forms a core and the polysiloxane is coated on the surface thereof, or it may equally have a structure in which single cores have agglomerated, i.e. in which metal fluoride particles are dispersed in an agglomerate of polysiloxane. It is preferred that the thickness of the polysiloxane coating on the metal fluoride particles is in the range of 0.1 to 100 μm, and further preferred that it is in the range of 1 to 50 μm. These ranges include all values and subranges therebetween.

The metal fluoride particles of the present invention can be used in any form such as particulate form, needle form, fibrous form or plate form. The particle size and particle size distribution are not particularly limiting and there are no particular limitations with respect thereto. Particle size and distribution are determined by conventional techniques. However, when the metal fluoride of the present invention is to be incorporated into a dental restorative resin, a particle size of 1 mm or less, in particular, 0.1 mm or less is preferred. Those ranges include all values and subranges therebetween.

The preferred size will depend on the intended application. For example, in the case that it is used in a dental filler, it is preferred that the size is 0.1 mm or less taking into consideration the affects on the strength and usability of the composition incorporating said fluoride compound.

When it is to be used in a dental adhesive, in particular, a cement, it is preferred that the size is 0.05 mm or less taking into consideration the affects on the film thickness and its strength. When it is used in a pit and fissure sealant, it is preferred that the size is 0.02 mm or less from the point of view of usability. Particles having small particle sizes have a large specific surface giving a large elution speed, but on the other hand tend to have a short elution time, and accordingly the size of the fluoride compound should thus be selected taking into consideration these factors.

The metal fluoride particle of the present invention has the same form as the inorganic powders such as viscosity increasing agents or fillers commonly incorporated into dental restorative resins, and can therefore be incorporated into a dental composition, which may include polymerizable monomers and polymerization initiators, using the same methods as those used for said fillers and viscosity increasing agents. The thus obtained dental composition can be used in the same way as conventionally known dental restorative resins such as dental adhesives, dental filling resins or pit and fissure sealants. The metal fluoride particle of the present invention may also have its surface subjected to conventionally known surface treatments.

In the dental composition, the metal fluoride is preferably used in an amount of 0.01 to 95 weight percent with respect to the polymerizable monomer, and preferably in an amount of 0.1 to 90 weight percent. These ranges include all values and subranges therebetween.

The type of polymerizable monomer used should be appropriately selected depending on the intended use. Preferable monomers include esters of α-cyanoacrylic acid, (meth)acrylic acid, α-haloacrylic acid, crotonic acid, cinnamic acid, sorbic acid, maleic acid, itaconic acid etc., (meth)acrylamide and derivatives thereof, vinyl esters, vinyl ethers, mono-N-vinyl derivatives, styrene derivatives etc. Of these, (meth)acrylic esters are preferably used.

Preferred examples of the polymerizable monomers are given below. In the present invention, acrylic and methacrylic equivalents are designated together by the prefix "(meth)acryl".

(I) Monofunctional monomers:
methyl (meth)acrylate, iso-butyl (meth)acrylate, benzyl (meth)acrylate, lauryl (meth)acrylate, 2-hydroxyethyl (meth)acrylate, 2-(N,N-dimethylamino) ethyl (meth) acrylate, 2,3-dibromopropyl (meth)acrylate, oxiranyl methyl (meth)acrylate and 3-methacryloyloxypropyl trimethoxy silane.

(II) Bifunctional monomers:
ethylene glycol di(meth)acrylate, triethylene glycol di(meth)acrylate, propylene glycol di(meth)acrylate, neopentyl glycol di(meth)acrylate, 1,6-hexanediol di(meth) acrylate, 1,10-docanediol di(meth)acrylate, bisphenol-A-di (meth)acrylate, 2,2-bis((meth)acryloyloxyethoxyphenyl) propane, 2,2-bis((meth)acryloyloxypolyethoxyphenyl) propane, 2,2-bis(4-(3-(meth)acryloxy-2-hydroxypropoxy) phenyl) propane, 1,2-bis (3-(meth)acryloyloxy-2-hydroxypropoxy) ethane etc.

(III) Trifunctional and higher functional monomers:
trimethylol propane tri(meth)acrylate, trimethylol ethane tri(meth)acrylate, tetramethylol methane tri(meth)acrylate, pentaerythritol tetra(meth)acrylate etc.

The above polymerizable monomers can be used singularly or in combinations of several types thereof.

Any kind of polymerization initiator can be used provided it can polymerize and cure the polymerizable monomers. Examples include benzoyl peroxide-aromatic tertiary amine polymerization initiators; peroxides such as cumene hydroperoxide; tributyl borane; and aromatic sulphinic acid (or salts thereof)-aromatic secondary or tertiary amine-acyl peroxide polymerization initiators. Other examples include photopolymerization initiators such as camphorquinone; camphorquinone-tertiary amine polymerization initiators, camphorquinone-aldehyde polymerization initiators; and camphorquinone-mercaptan polymerization initiators.

Preferably, the fluoride ion releasing composition of the present invention may also include polymerizable monomers having acidic groups to further enhance adhesiveness between the tooth substrate and the restorative material. Preferably, these acidic groups may be phosphoric acid residues, pyrophosphoric acid residues, thiophosphoric acid residues; or carboxylic acid residues. Preferred examples of said compounds are given below.

Examples of polymerizable monomers having phosphoric acid residues include: 2-(meth)acryloyloxyethyl dihydrogenphosphate, 10-(meth)acryloyloxydecyl dihydrogenphosphate, 20-(meth)acryloylloxyeicosyl dihydrogenphosphate, 1,3 -di(meth)acryloyloxypropyl-2-dihydrogen phosphate, 2-(meth)acryloyloxyethyl phenyl phosphoric acid, 2-(meth)acryloyloxyethyl 2'-bromoethyl phosphoric acid, (meth)acryloyloxyethyl phenylphosphonate etc. and acid chlorides thereof.

Examples of polymerizable monomers having pyrophosphoric acid residues include: di (2-(meth)acryloyl oxyethyl) pyrophosphate etc. and acid chlorides thereof.

Examples of polymerizable monomers having thiophosphoric acid residues include: 2-(meth)acryloyl oxyethyl dihydrogen dithiophosphate, 10-(meth)acryloyl oxydecyl dihydrogen thiophosphate etc. and acid chlorides thereof.

Examples of polymerizable monomers having carboxylic acid residues include: 4-(meth)acryloyloxyethoxycarbonylphthalic acid, 4-(meth)acryloyl oxyethoxycarbonylphthalic anhydride, 5-(meth)acryloyl aminopentyl carboxylic acid, 11-(meth)acryloyl oxy-1,1-undecane carboxylic acid and acid chlorides thereof, Other fillers can also be added to the fluorine releasing composition of the present invention. Examples of fillers include: clay minerals such as quartz, glass, hydroxyapatite, calcium carbonate, barium sulphate, titanium oxide, zirconium oxide, ceramics, diatomaceous earth, kaolin, montmorillonite etc.; inorganic fillers such as activated china clay, synthetic zeolite, mica, calcium phosphate, fluoroaluminosilicate, microparticulate silica, microparticulate alumina etc.; organic fillers such as polymethylmethacrylate, polymers of multifunctional acrylates, polyamides, polyesters, polystyrene, polyvinyl chloride, chloroprene rubber, nitrile rubber, styrene-butadiene rubber etc.; the above inorganic fillers coated with the above-mentioned organic fillers; or inorganic/organic complex fillers such as ones including the above-mentioned organic fillers having the above-mentioned inorganic fillers dispersed therein.

In addition to the above-mentioned components, the composition of the present invention may also include organic solvents, polymerization inhibitors, antioxidants, U.V. absorbers, pigments, dyes etc. added thereto where practically necessary.

A dental composition having the fluoride particle of the present invention incorporated therein can be used in composite resins for filling cavities; lining agents for coating cavities, adhesives for bonding inlays, onlays and crowns etc., to cavities or abutment teeth; adhesives for orthodontic treatments; adhesives for supporting bridges, posts etc.; and fissure sealants. Whilst on the one hand it acts to strengthen tooth substrate through the active release of fluoride ions, there is also no accompanying reduction in the mechanical properties or adhesion performance of the dental composition whereby its function as a dental restorative resin can be maintained.

EXAMPLES

Having generally described this invention, a further understanding of the present invention can be obtained by reference to certain specific examples, which are provided herein for purposed of illustration only, and are not intended to be limiting thereof.

Example 1

To 34.7 g of tetraethoxysilane were added 12 g (which is the molar equivalent with respect to the ethoxy groups) of water, 10 g of ethanol, and 0.02 g of hydrochloric acid. The resulting mixture was then subjected to thermal reflux for 2 hours whilst stirring to hydrolyze the tetraethoxysilane.

To this solution was added 10 g of sodium fluoride powder, and after stirring the ethanol was distilled off under vacuum. It was then heated at 120° C. for 30 minutes to obtain 19 g of a white powder.

There was no elution of silane compounds into the washing liquid upon washing with ethyl acetate, whereby it was confirmed that the tetraethoxysilane had after hydrolysis become polymerized by condensation on the surface of the sodium fluoride and become insoluble.

Comparison of the infrared absorption spectra of the obtained fluoride compound with that of tetraethoxysilane showed that the absorption of ethoxy groups of the tetraethoxysilane at 960, 1170 $cm^{-1}$ had disappeared, and that a broad $SiO_2$ absorption had appeared at around 1000–1200 $cm^{-1}$, whereby it was confirmed that the tetraethoxysilane had polymerized after hydrolysis to form a polysiloxane structure, and that sodium fluoride coated with polysiloxane had been produced.

Examples 2–4

The silane compounds and metal fluorides shown in Table 1 and the same methods as in Example 1 were used. The alkoxysilane was hydrolyzed and then coated onto the surface of the metal fluoride, whereafter it was subjected to condensation to obtain a fluoride compound comprised of a metal fluoride coated with polysiloxane.

Example 5

A liquid mixture of 100 g of vinyl triethoxy silane and 100 g of water were added to 0.2 g of acetic sold, and then stirred at room to temperature until the system became homogenous. Saturated salt solution was added to this aqueous solution followed by extraction with ethyl acetate. The ethyl acetate solution was then washed with an aqueous solution of sodium hydrogen carbonate to remove acetic acid. The ethyl acetate solution was then dried with anhydrous sodium sulphate and anhydrous magnesium, sulphate. When the drying agents were removed by filtering and the ethyl acetate was distilled off by vacuum distillation, 23 g of hydrolyzed vinyl triethoxy silane was produced.

10 g of this hydrolyzed vinyl triethoxy silane was dissolved into 10 g of toluene, and then 0.5 g of 3-aminopropyl triethoxysilane were added as a curing catalyst.

11

This solution was then added to 10 g of sodium fluoride powder. After stirring, the toluene was distilled off under vacuum, followed by heating for 30 minutes at 120° C. to obtain 19 g of a white powder.

There was no elution of silane compound into the washing liquid upon washing with toluene, whereby it was confirmed that the vinyltriethoxysilane had after hydrolysis become polymerized by condensation on the surface of the sodium fluoride and become insoluble.

Furthermore, comparison of the infrared absorption spectra of the fluoride compound with that of vinyl triethoxysilane showed that the absorption of ethoxy groups of the vinyl triethoxysilane at 950, 1170 cm$^{-1}$ had disappeared, and that a broad $SiO_2$ absorption had appeared at around 1000-200 cm$^{31\ 1}$, whereby it was confirmed that the vinyl triethoxysilane had polymerized after hydrolysis to form a polysiloxane structure, and that sodium fluoride coated with polysiloxane had bean produced.

Example 6

The silane compound and metal fluoride shown in Table 1 and the same methods as in Example 1 were used. The alkoxysilane was hydrolyzed and then coated onto the surface of the metal fluoride. It was then subjected to condensation to produce metal fluoride coated with polysiloxane.

Examples 7–10

The silane compounds and metal fluorides shown in Table 1 and the same methods as in Example 5 were used. The alkoxysilane was hydrolyzed and then coated onto the surface of the metal fluoride. It was then subjected to condensation to produce metal fluoride coated with polysiloxane.

Example 11

The silane compound and metal fluoride shown in Table 1 and the same methods as in Example 1 were used. The alkoxysilane was hydrolyzed and then coated onto the surface of the metal fluoride. It was then subjected to condensation to produce metal fluoride coated with polysiloxane.

Example 12

The silane compound and metal fluoride shown in Table 1 and the same methods as in Example 5 were used. The alkoxysilane was hydrolyzed and then coated onto the surface of the metal fluoride. It was then subjected to condensation to produce metal fluoride coated with polysiloxane.

Example 13

10 g of siloxane oligomer (MSAC made by Kabushiki Kaishe Mitsubishi Kagaku) were dissolved in 10 g of toluene, and then 0.1 g of nitric acid were added as a curing catalyst.

This solution was then added to 10 g of sodium fluoride powder. After stirring, the toluene was distilled off under vacuum followed by heating at 120° C. for 30 minutes to obtain 18 g of a white powder.

No elution of silane compound was observed upon washing with toluene, whereby it was confirmed that the siloxane oligomer had undergone cross-linking and that sodium fluoride coated with polysiloxane had been produced,

Example 14

The silane compound and metal fluoride shown in Table 1 and the came methods as in Example 13 were used. The siloxane oligomer was coated onto the surface of the metal fluoride. It was then subjected to condensation to produce metal fluoride coated with polysiloxane.

Reference Example 1

10 g of 3-methacryloyloxypropyl trimethoxy silane was dissolved in 10 g of toluene, and then this solution was added to 10 g of sodium fluoride powder followed by stirring. Thereafter, the toluene was distilled off under vacuum followed by heating at 120° C. to produce 18 g of sodium fluoride surface-treated with 3-methacryloyloxypropyl trimethoxy silane.

Reference Example 2

10 g a mixture made up of 50 parts by weight of 2,2-bis (4-3-methacryloloxy-2-hydroxypropoxy) phenyl) propane (Bis-GMA), 50 parts by weight of 1,6-hexanediol dimethacrylate and 1 part by weight of benzoyl peroxide were dissolved in 10 g of toluene, and this solution was added to 10 g of sodium fluoride powder followed by stirring. The toluene was then distilled off under vacuum followed by heating at 120° C. for 3 hours to produce 18 g of sodium fluoride coated with methacrylic resin.

Reference Example 3

10 g of polyethylene glycol (PEG: molecular weight: 15000–25000) was dissolved in methanol, and then this solution was added to 10 g of sodium fluoride followed by stirring. The methanol was then distilled off under vacuum to produce 18 g of sodium fluoride coated with PEG.

Examples 15–28 and Comparative Examples 1–6

The following compositions A and B were prepared. Compositions A-1, A-2, A-3, A-4, A-5, A-6, A-7, A-8, A-9, A-10, A-11, A-12, A-13 and A-14 were then prepared by respectively mixing the metal fluoride compounds produced in Examples 1–14 with 100 parts by weight of composition A such that the amount of the incorporated pure metal fluoride (not including the coating) was 5 parts by weight. These compositions were then used to measure the durability of adhesion to metal.

| Composition A | |
|---|---|
| Bis-GMA | 40 parts by weight |
| Triethylene glycol dimethacrylate | 40 parts by weight |
| 10-Methacryloyloxydecyl dihydrogenphosphate | 20 parts by weight |
| Benzoyl peroxide | 2 parts by weight |
| Silane treated quartz powder | 300 parts by weight |
| Composition B | |
| Bis-GMA | 40 parts by weight |
| Triethyleneglycol dimethacrylate | 30 parts by weight |
| 2-hydroxyethyl methacrylate | 30 parts by weight |
| Sodium 2,4,6-triisopropyl benzene sulphinate | 1 part by weight |
| N,N-diethanol-p-toluidine | 2 parts by weight |
| Silane treated quartz powder | 300 parts by weight |

A nickel chrome alloy (Nowchrom (I) made by Towa Giken) was ground to smoothness with 1000 grit silicon carbide paper, and then adhesive tape having a 5 mm diameter (ϕ) hole formed therein was stuck onto the resulting smooth surface, and this was adopted as the surface for adhesion. At the same time, a cylindrical rod made from stainless steel (SUS304) having dimensions of 25 mm×7 mmφ was prepared, and one end thereof was subjected to sandblasting with alumina abrasive grains having a grain size of 50 μm. Next, compositions A-1, A-2, A-3, A-4, A-5, A-6, A-7 A-8, A-9, A-10, A-11, A-12, A-13 and A-14 were each kneaded together with an equal amount of composition B, and then the resulting mixtures were each applied onto the sandblasted surface of the cylindrical rod which was then pressed onto the surface of the alloy prepared for adhesion to thereby adhere the two together. After 1 hour, the adhered samples were immersed in water at 37° C. Eight test pieces were immersed in water at 37° C. for 24 hours and then tested to measure the strength of adhesion, and another eight test pieces were first immersed in water at 37° C. for 24 hours and then immersed in water at 70° C. for one month before being tested to measure the strength of adhesion. The strength of adhesion was measured using a universal testing machine (made by Instron) wherein the tensile bond strength wits measured at a cross head speed of 2 mm/min. The measured values were averaged out for each sample and are shown in Table 2.

Composition A without any fluoride compound incorporated, composition A-15 having 5 parts by weight of sodium fluoride without any polysiloxane coating added to 100 parts by weight of composition A; and composition A-16 having 5 parts by weight of calcium fluoride without any polysiloxane coating added to 100 parts by weight of composition A were each tested in the same way as Examples 15–28 to measure the durability of adhesion to metal. They were respectively adopted as Comparative Examples 1, 2 and 3, and the results are shown together in Table 2.

Further compositions A-17, A-18 and A-19 were prepared by taking composition A and respectively adding thereto the fluoride compound of Reference Example 1 whose surface had not been coated with polysiloxane but only treated with a silane coupling agent; the fluoride compound of Reference Example 2 whose surface had not been coated with polysiloxane but with polymethacrylate; and the fluoride compound of Reference Example 3 whose surface had been coated with PEG, in an amount such that the amount of metal fluoride compound incorporated was 5 parts by weight. These three compositions were each tested in the same way as Examples 15–28 to measure the durability of adhesion to metal. They were adopted as Comparative Examples 4, 5 and 6, and the results are shown together in Table 2.

The composition including a metal fluoride compound without any polysiloxane coating, the compositions including the fluoride compound of the reference examples which had only been surface-treated with a silane coupling agent, and the composition including fluoride compound which had been coated with PEG were each shown by the durability test to display a remarkable decrease in adhesion strength, whereas the compositions including fluoride compounds comprising metal fluoride whose surface had been coated with polysiloxane showed only a small decrease in adhesion strength.

Examples 29–32 and Comparative Examples 7–9

The following composition C was prepared. Compositions C-1, C-2, C-3 and C-4 were prepared by adding to 100 parts of composition C the metal fluoride compounds obtained in Examples 1, 2, 5 and 13 respectively such that the amount thereof incorporated was 10 parts by weight. The durability of bending strength of the cured products thereof was measured.

| Composition C | |
|---|---|
| Bis-GMA | 50 parts by weight |
| Triethylene glycol dimethacrylate | 50 parts by weight |
| Camphorquinone | 1 part by weight |
| Ethyl ester of p-N,N-dimethylaminobenzoate | 1 part by weight |
| Silane treated quartz powder | 300 parts by weight |
| Silane treated colloidal silica | 5 parts by weight |

The above-described compositions C-1, C-2, C-3 and C-4 were loaded into a mold having a length of 30 mm, a height of 2 mm and a width of 2 mm, and then irradiated with a dental visible light irradiator "LIGHTEL II" made by Kabushiki Kaisha Gunma Ushio Denki to prepare cured products. Test pieces were then immersed in water at 37° C. Eight test pieces were immersed in water at 37° C. for 24 hours and then tested to measure the bending strength. Another eight test pieces were first immersed in water at 37° C. for 24 hours and then further immersed in water at 70° C. for 1 month before being tested to measure the bending strength. The bending strength test was effected using a universal testing machine (made by Instron) at a cross head speed of 1 mm/min. The series of measured values for each composition were averaged out, and the results are shown in Table 3.

Composition C including no fluoride compound; composition C-5 including sodium fluoride; and composition C-6 including the fluoride compound of Reference Example 1 whose surface had not been coated with polysiloxane but only surface-treated with a silane coupling agent were each tested in the same way as Examples 29–32. They were adopted as Comparative Examples 7–9, and the results are shown together in Table 3.

Whereas the compositions including metal fluoride compounds without any polysiloxane coating and the compositions including the fluoride compounds of the reference examples displayed a remarkable decrease in bending strength, the compositions including metal fluorides which had been coated with polysiloxane compounds displayed only a small decrease in bending strength.

Examples 33–37 and Comparative Examples 10–12

The following composition D was prepared. Compositions D-1, D-2, D-3, D-4 and D-5 were prepared by adding to 100 parts of composition D the metal fluoride compounds obtained in Examples 1, 2, 5, 12 and 13 respectively such that the amount of pure metal fluoride incorporated was 5 parts by weight. The durability of the strength of adhesion of these compositions to tooth substrate was measured.

| Composition D | |
|---|---|
| Bis-GMA | 40 parts by weight |
| 1,6-hexanediol dimethacrylate | 20 parts by weight |
| 2-hydroxyethyl methacrylate | 30 parts by weight |
| 10-methacryloyloxydecyl dihydrogenphosphate | 10 parts by weight |
| Camphorquinone | 1 part by weight |
| DMAEMA* | 1 part by weight |
| Colloidal silica | 10 parts by weight |

*DMAEMA is N,N-dimethylaminoethyl methacrylate.

A human molar tooth was ground with 1000 grit silicon carbide paper to form a smooth dentin surface. Adhesive tape formed with a 3 mmφ hole therein was applied to this surface, and this was adopted as the surface for adhesion.

The surface for adhesion was then coated with tooth surface conditioner "Clearfil® LB primer" (made by Kabushiki Kaisha Kuraray) and then dried using an air syringe after being left for 30 seconds. Compositions D-1, D-2, D-3, D-4 and D-5 were then coated to a thickness of 100 microns onto the coating of primer using a small brush followed by irradiation with light for 20 seconds using a dental light irradiator "LIGHTEL II" (made by Kabushiki Kaisha Gunme Ushio Denki) to cure the composition. Next, a commercially available photopolymerization type dental composite resin, "Photo Clearfil® A" (made by Kabushiki Kaisha Kuraray) was laid thereon and cured by irradiation with light for 40 seconds using the above-mentioned light irradiator.

This cured product was then adhered to a stainless steel (SUS304) cylindrical rod having dimensions of 7 mmφ×25 mm using a commercially available dental resin cement "Panavla® 21"(made by Kabushiki Kaishe Kuraray). After 1 hour, a total of 16 test pieces were immersed into water at 37° C. Of these 16 test places, 8 were immersed in water at 37° C. for 24 hours and then tested to measure the adhesion strength. The remaining eight test pieces were first immersed in water at 37° C. for 24 hours and then subjected 4000 times to a heat cycle involving immersion in cold water at 4° C. for one minute and then warm water at 60° C. for one minute. The adhesion strength was measured by using a universal testing machine (made by Instron) to measure the tensile bond strength at a cross head speed of 2 mm/min. The series of measured values were averaged out for each composition and the results are shown in Table 4.

Composition D which includes no fluoride compound; composition D-6 which includes sodium fluoride; and composition D-7 which includes the fluoride compound of Reference Example 2 whose surface had not been coated with polysiloxane but only surface-treated with a silane coupling agent, were each tested in the some way as Examples 33–37. They were adopted as Comparative Examples 10–12 respectively, and the results are shown together in Table 4.

Those compositions including metal fluoride which had not been coated with polysiloxane, and those compositions including the fluoride compounds of the reference examples displayed a remarkable decrease in adhesion strength after being subjected to the heat cycle; whereas those compositions including metal fluoride compounds which had been coated with polysiloxane displayed only a small decrease in adhesion strength.

Examples 38–41 and Comparative Examples 13–15

Compositions A-1, A-5, A-6 and A-13, which were used in Examples 15, 19, 20 and 27 respectively, were each kneaded together with an equal amount of composition B.

A mold was then used to prepare disc-shaped cured products having a diameter of 2 cm and a thickness of 1 mm. These products were then immersed in 4 ml of phosphoric acid buffer solution (pH 7) at 37° C., and the amount of fluoride ions that was eluted from the disc-shaped cured products was measured. Determination was carried out using a fluoride ion electrode (made by Orion Research Company). The results of measurement of the amount of eluted fluoride ions are shown in FIG. 1.

Composition A which was used in Comparative Example 1 and includes no fluoride compound, composition A-15 which was used in Comparative Example 2 and includes 5 parts by weight of sodium fluoride, and composition A-18 which includes the fluoride compound of Reference Example 2 which comprises sodium fluoride whose surface has been coated with polymethacrylate, were tested in the same way as Examples 38–41. They were adopted as Comparative Examples 13–15 respectively and the results are shown together in FIG. 1.

It has beam confirmed that the act of coating the metal fluoride with a polysiloxane compound does not cause a decrease in the amount of fluoride ions eluted but rather causes an increase in the same. On the other hand, when polymethacrylate and not polysiloxane was used as the coating material, the act of coating the metal fluoride caused a decrease in the amount of fluoride ions eluted.

Examples 42–45

The following test was carried out in order to show the relationship between the particle size of the fluoride compound and effect of the present invention, The metal fluoride compound coated with polysiloxane which was prepared in Example 13 was subjected to sieving with #150 mesh to separate the fine particles and rough particles Compositions were prepared in the same way as Example 27 except that the above-mentioned separated fine particles and rough particles of metal fluoride compound were respectively used instead of the metal fluoride compound of Example 13. The examples were subjected to an adhesion test in the same way as Example 27, and the following measurements were achieved after 30 days at 70° C.:

fine particles (Example 42): 30.8 MPa rough particles (Example 43): 32.4 MPa

Further compositions were prepared in the same way as Example 41 except that the above-mentioned separated fine particles and rough particles of metal fluoride compound were respectively used instead of the metal fluoride compound of Example 13. The examples were tested in the same way as Example 41, with the result that each showed a fluoride ion releasing action similar to that of Example 41 (Examples 44 and 45). It is therefore clear that the effect of the present invention is not due to the particle size.

In a fluoride ion releasing dental composition, the incorporation of a fluoride particle obtained by coating a metal fluoride particle with a polysiloxane compound can substantially solve the problem of reduction in mechanical properties and adhesion performance associated with the elution of fluoride ions.

In this way, a large increase in the durability of the mechanical properties and adhesion performance can be realized with the composition of the present invention in comparison with conventional compositions, and the practical value thereof is thus extremely high.

The fluoride ion releasing dental composition of the present invention can be used, for example, as a dental adhesive, a dental filling resin, a composite resin for core build-up, or a fissure sealant.

TABLE 1

|  | Raw Material of Coating Material | Metal Fluoride | Proportion of polysiloxane compound to 100 parts by weight of metal fluoride (parts by weight) |
| --- | --- | --- | --- |
| Example 1 | Tetraethoxysilane | Sodium fluoride | 100 |
| Example 2 | Tetraethoxysilane | Calcium fluoride | 300 |

TABLE 1-continued

| | Raw Material of Coating Material | Metal Fluoride | Proportion of polysiloxane compound to 100 parts by weight of metal fluoride (parts by weight) |
|---|---|---|---|
| Example 3 | Tetramethoxysilane | Sodium fluoride | 200 |
| Example 4 | Tetraethoxysilane | Sodium fluoride | 10 |
| Example 5 | Vinyl triethoxysilane | Sodium fluoride | 100 |
| Example 6 | Methyl triethoxysilane | Sodium fluoride | 200 |
| Example 7 | Methyl triethoxysilane | Sodium fluoride | 700 |
| Example 8 | Ethyl triethoxysilane | Calcium fluoride | 25 |
| Example 9 | Hexyl trimethoxysilane | Tin fluoride | 500 |
| Example 10 | Phenyl triethoxysilane | Strontium fluoride | 200 |
| Example 11 | Tetraethoxysilane | Sodium fluoride | 100 |
| | Vinyl triethoxysilane | | 100 |
| Example 12 | Propyl triethoxysilane | Titanium potassium fluoride | 100 |
| Example 13 | MSAC | Sodium fluoride | 200 |
| Example 14 | MSAC | Strontium fluoride | 50 |
| Ref. Example 1 | 3-methacryloyloxy trimethoxysilane | Sodium fluoride | 100 |
| Ref. Example 2 | Bis-GMA, 1-6-hexanediol dimethacrylate, Benzoyl peroxide | Sodium fluoride | 100 |
| Ref. Example 3 | Polyethylene glycol | Sodium fluoride | 100 |

MSAC: Organosiloxane oligomer (made by Kabushiki Kaisha Mitsubishi Kageku)

TABLE 2

| | | Tensile bond strength (MPa) | |
|---|---|---|---|
| | Fluoride Compound | After 24th at 37° C. | After 30 days at 70° C. |
| Example 15 | Example 1 | 31.1 | 28.2 |
| Example 16 | Example 2 | 30.3 | 29.6 |
| Example 17 | Example 3 | 27.5 | 27.3 |
| Example 18 | Example 4 | 26.3 | 10.6 |
| Example 19 | Example 5 | 30.5 | 26.5 |
| Example 20 | Example 6 | 27.7 | 26.3 |
| Example 21 | Example 7 | 27.2 | 27.9 |
| Example 22 | Example 8 | 28.9 | 19.0 |
| Example 23 | Example 9 | 27.1 | 22.7 |
| Example 24 | Example 10 | 28.2 | 26.1 |
| Example 25 | Example 11 | 27.6 | 28.0 |
| Example 26 | Example 12 | 29.6 | 27.2 |
| Example 27 | Example 13 | 33.0 | 31.8 |
| Example 28 | Example 14 | 32.6 | 28.0 |
| Comp. Example 1 | None | 30.1 | 27.8 |
| Comp. Example 2 | Sodium fluoride | 30.7 | 1.9 |
| Comp. Example 3 | Calcium fluoride | 27.6 | 2.8 |
| Comp. Example 4 | Reference example 1 | 29.8 | 4.5 |
| Comp. Example 5 | Reference example 2 | 30.4 | 15.5 |
| Comp. Example 6 | Reference example 3 | 26.8 | 0.0 |

TABLE 3

| | | Bending strength (MPa) | |
|---|---|---|---|
| | Fluoride Compound | After 24th at 37° C. | After 30 days at 70° C. |
| Example 29 | Example 1 | 178 | 160 |
| Example 30 | Example 2 | 173 | 153 |
| Example 31 | Example 5 | 189 | 158 |
| Example 32 | Example 13 | 175 | 155 |
| Comp. Example 7 | None | 182 | 161 |
| Comp. Example 8 | Sodium fluoride | 168 | 31 |
| Comp. Example 9 | Reference Example 1 | 172 | 38 |

TABLE 4

| | | Tensile bond strength (MPa) | |
|---|---|---|---|
| | Fluoride Compound | After 24th at 37° C. | After heat cycle |
| Example 33 | Example 1 | 21.9 | 19.2 |
| Example 34 | Example 2 | 19.9 | 17.2 |
| Example 35 | Example 5 | 20.0 | 17.9 |
| Example 36 | Example 12 | 19.3 | 19.0 |
| Example 37 | Example 13 | 19.9 | 17.2 |
| Comp. Example 10 | None | 21.8 | 19.2 |
| Comp. Example 11 | Sodium fluoride | 18.2 | 5.3 |
| Comp. Example 12 | Reference Example 1 | 18.4 | 6.5 |

Obviously, numerous modifications and variations of the present invention are possible in light of the above teachings. It is therefore to be understood that within the scope of the appended claims, the invention may be practiced otherwise than as specifically described herein.

This application is based on Japanese Patent Application 8-196025 (1996) filed Jul. 25, 1996, the entire contents of which are hereby incorporated by reference.

What is claimed as new and desired to be secured by Letters Patent of the United States is:

1. A coated particle, comprising:
   (i) a particle comprising a metal fluoride soluble in water and releasing fluoride ions; and
   (ii) a coating on the surface of said particle, said coating comprising a polysiloxane.

2. The coated particle according to claim 1, wherein said metal fluoride is selected from the group consisting of lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, diamine silver fluoride, sodium hydrogen fluoride, potassium hydrogen fluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorodistannate (II), and potassium hexafluorozirconate.

3. The coated particle according to claim 2, wherein said metal fluoride is selected from the group consisting of lithium fluoride, sodium fluoride, potassium fluoride, calcium fluoride, and strontium fluoride.

4. The coated particle according to claim 1, wherein said coating has a thickness of 0.1–100 $\mu$m on the surface of said particle.

5. A coated particle, comprising:

a particle comprising a metal fluoride soluble in water and releasing fluoride ions; and a coating of a reaction product of a silanol compound obtained by hydrolysis or partial hydrolysis of a silane compound having the general formula (I):

$$[(R^1O)_l(X)_m]_{4-n}\text{—}SiR^2{}_n \qquad (I)$$

wherein $R^1$ is an organic group having no more than 8 carbons, X is a halogen, $R^2$ is an organic group having no more than 6 carbon atoms, l and m are integers 0 or 1, whose sum is 1, and n is an integer of 0 or 1.

6. The coated particle according to claim 5, wherein the reaction product comprises a crosslinked polysiloxane or organopolysiloxane on the surface of said particle.

7. The coated particle according to claim 5, wherein said metal fluoride is selected from the group consisting of lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, diamine silver fluoride, sodium hydrogen fluoride, potassium hydrogen fluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorodistannate (II), and potassium hexafluorozirconate.

8. The coated particle according to claim 7, wherein said metal fluoride is selected from the group consisting of lithium fluoride, sodium fluoride, potassium fluoride, calcium fluoride, and strontium fluoride.

9. The coated particle according to claim 6, wherein said polysiloxane or organopolysiloxane has a thickness of 0.1–100 μm on the surface of said particle.

10. A method, comprising:

contacting a particle comprising a metal fluoride soluble in water and releasing fluoride ions with a silanol compound obtained by hydrolysis or partial hydrolysis of a silane compound having the general formula (I):

$$[(R^1O)_l(X)_m]_{4-n}\text{—}SiR^2{}_n \qquad (I)$$

wherein $R^1$ is an organic group having no more than 8 carbons, X is a halogen, $R^2$ is an organic group having no more than 6 carbon atoms, l and m are integers 0 or 1, whose sum is 1, and n is an integer of 0 or 1; and allowing said silanol to undergo a condensation reaction.

11. The method according to claim 10, further comprising:

contacting the obtained coated particle with a dental composition comprising a polymerizable monomer and a polymerization initiator.

12. The method according to claim 11, further comprising:

contacting the obtained dental composition with a tooth.

13. The method according to claim 10, wherein said metal fluoride is selected from the group consisting of lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, diamine silver fluoride, ammonium fluoride, sodium hydrogen fluoride, ammonium hydrogen fluoride, potassium hydrogen fluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorodistannate (II), and potassium hexafluorozirconate.

14. The method according to claim 13, wherein said metal fluoride is selected from the group consisting of lithium fluoride, sodium fluoride, potassium fluoride, calcium fluoride, and strontium fluoride.

15. A dental composition, comprising the coated particle as claimed in claim 1.

16. The dental composition according to claim 15, further comprising a polymerizable monomer and a polymerization initiator.

17. A dental composition, comprising the coated particle as claimed in claim 5.

18. The dental composition according to claim 17, further comprising a polymerizable monomer and a polymerization initiator.

19. A method, comprising:

contacting a particle comprising a metal fluoride soluble in water and releasing fluoride ions with silanol oligomers obtained by condensation of a silane compound having the general formula (I)

$$[(R^1O)_l(X)_m]_{4-n}\text{—}SiR^2{}_n \qquad (I)$$

wherein $R^1$ is an organic group having no more than 8 carbons, X is a halogen, $R^2$ is an organic group having no more than 6 carbon atoms, l and m are integers 0 or 1, whose sum is 1, and n is an integer of 0 or 1; and allowing said oligomers to undergo a condensation reaction.

* * * * *